United States Patent
Fehr

(10) Patent No.: US 8,227,629 B2
(45) Date of Patent: Jul. 24, 2012

(54) PROCESS FOR THE PREPARATION OF TETRANORLABDANE DERIVATIVES

(75) Inventor: Charles Fehr, Versoix (CH)

(73) Assignee: Firmenich SA, Geneva (CH)

( * ) Notice: Subject to any disclaimer, the term of this patent is extended or adjusted under 35 U.S.C. 154(b) by 291 days.

(21) Appl. No.: 12/680,244

(22) PCT Filed: Oct. 20, 2008

(86) PCT No.: PCT/IB2008/054298
§ 371 (c)(1),
(2), (4) Date: Mar. 26, 2010

(87) PCT Pub. No.: WO2009/053883
PCT Pub. Date: Apr. 30, 2009

(65) Prior Publication Data
US 2010/0311990 A1    Dec. 9, 2010

(30) Foreign Application Priority Data
Oct. 23, 2007  (EP) .................................. 07119037

(51) Int. Cl.
C07D 307/92  (2006.01)
C07C 33/14   (2006.01)
C07C 47/225  (2006.01)
(52) U.S. Cl. ..................... 549/458; 568/445; 568/819
(58) Field of Classification Search .................. 549/458; 568/445, 819
See application file for complete search history.

(56) References Cited

FOREIGN PATENT DOCUMENTS

| WO | WO 02/22526 A2 | 3/2002 |
|---|---|---|
| WO | WO 02/40155 A1 | 5/2002 |
| WO | WO 2004/013069 A1 | 2/2004 |
| WO | WO 2006/010287 A1 | 2/2006 |
| WO | WO 2007/010420 A1 | 1/2007 |

OTHER PUBLICATIONS

Daniewski et al., "High-Pressure Approach to the Total Synthesis of (±)-Ambreinolide and (±)-8-Epiambreinolide," J. Org. Chem., 50:3963-3965 (1985).
Erman et al., "The Rearrangement of Tertiary Propargyl Alcohols to $d,\beta$-Unsaturated Aldehydes in the Presence of Polymeric Organosilyl Vanadates," Tetrahedron Letters, 34:2981-2984 (1976).
Escher et al., "Configuration-Odor Relationships in 5β-Ambrox," Helvetica Chimica Acta, 73(7):1935-1947 (1990).
Fehr et al., "Copper-Catalyzed Cycloisomerizations of 5-En-1-yn-3-ols," Organic Letters, 8(9):1839-1841 (2006).
Fehr et al., "Stereoselective Synthesis of Superambrox: Stereoselective Type III Intramolecular Ene Reaction and OH-Assisted Ru-Catalyzed Isomerization," Angew. Chem. Int. Ed. 45(41):6904-6907 (2006).
Lorber et al., "Cis-dioxomolybdenum(VI) Complexes as New Catalysts for the Meyer-Schuster Rearrangement," Tetrahedron Letters, 37(6):853-856 (1996).
Noyori et al., "Asymmetric Transfer Hydrogenation Catalyzed by Chiral Ruthenium Complexes," Acc. Chem. Res. 30:97-102 (1997).
Noyori et al., "Asymmetric Catalysis by Architectural and Functional Molecular Engineering: Practical Chemo- and Stereoselective Hydrogenation of Ketones," Angew. Chem. Int. Ed. 40:40-73 (2001).
Verstegen-Haaksma et al., "Total Synthesis of (−)-Ambrox® from S-(+)-Carvone (part 6)," Tetrahedron, 50(33):10095-10106 (1994).
International Search Report and the Written Opinion of the International Searching Authority, Application No. PCT/IB2008/054298, Feb. 27, 2009.

Primary Examiner — Bernard Dentz
(74) Attorney, Agent, or Firm — Winston & Strawn LLP

(57) ABSTRACT

The present invention concerns a process for the preparation of a compound of formula (I), wherein the dotted line is a single bond and n is 1 or the dotted line is a double bond and n is 0, and wherein the relative configuration is as shown, in the form of any one of its diastereoisomers or enantiomers or mixtures thereof.

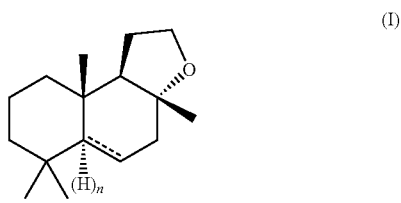

(I)

12 Claims, No Drawings

PROCESS FOR THE PREPARATION OF TETRANORLABDANE DERIVATIVES

This application is a 371 filing of International Patent Application PCT/IB2008/054298, filed Oct. 20, 2008.

TECHNICAL FIELD

The present invention relates to the field of organic synthesis and more specifically it concerns a process for the preparation of a compound of formula

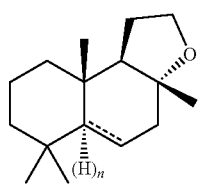

(I)

wherein the dotted line is a single bond and n is 1 or the dotted line is a double bond and n is 0, and wherein the relative configuration is as shown, in the form of any one of its diastereoisomers or enantiomer or mixture thereof. The invention concerns also some intermediates.

PRIOR ART

The compounds of formula (I) are very well known perfuming ingredients, some of which of particular relevance. Therefore, there is always a need for alternative synthesis to produce them.

To the best of our knowledge, the reported synthesis proceed in general through the cyclisation of an acid

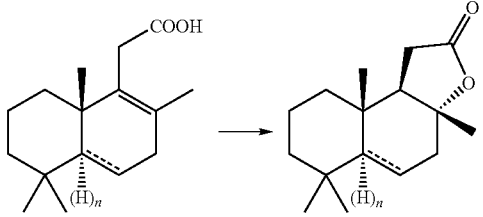

for instance see WO 04/013069. However, this procedure requires reduction of the subsequent lactone into a diol and then again a cyclisation step of the diol, which is quite heavy to handle.

Another approach reported in the prior art proceeds via the proton-promoted cyclisation of an unsaturated alcohol similar to our compound (IV), see WO 06/10287 or A. De Groot et al, in *Tetrahedron*, 1994, 50, 10095. However, these procedures require very long and tedious (industrially not feasible) preparation of the unsaturated alcohol, or the preparation of an ester and its subsequent reduction into the alcohol, as shown above. This method implies heavy chemistry and poor atom economy.

To the best of our knowledge, it is the first time that is reported an effective, short, atom economic preparation of compounds (I) with a propargylic alcohol (II), accessible in only three steps from commercial materials (C. Fehr et al, in *Angew. Chem. Int. Ed.*, 2006, 6904). A precedent attempt reported in the prior art using a propargylic alcohol failed (e.g. see C. Fehr et al, in *Org. Lett.*, 2006, 1840).

DESCRIPTION OF THE INVENTION

We have now found that a compound of formula (I) as defined below, e.g. (3aRS,9aRS,9bRS)-3a,6,6,9a-tetramethyl-1,2,3a,4,6,7,8,9,9a,9b-decahydronaphtho[2,1-b]furan or (3aRS,9aRS,9bRS)-3a,6,6,9a-tetramethyl-1,2,3a,4,6,7,8,9,9a,9b-decahydronaphtho[2,1-b]furan, can be produced in an advantageous manner by a new and alternative process comprising a propargylic rearrangement and a cyclisation step.

Therefore, a first object of the present invention is a process for the preparation of a furan of formula

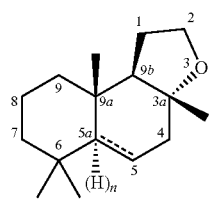

(I)

wherein the dotted line is a single bond and n is 1 or the dotted line is a double bond and n is 0, in the form of a racemic or optically active diastereoisomer, wherein the substituents in the positions 9a, 9b and 3a are in a relative configuration cis, and the hydrogen atom in position 5a and the oxygen atoms are in configuration trans relative to the methyl in position 9a; said process comprising the following steps:

A) the rearrangement of a propargylic alcohol of formula

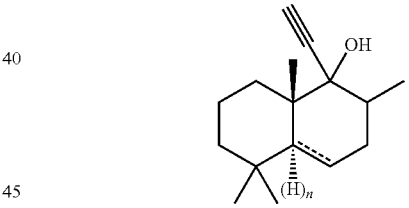

(II)

wherein the dotted line and n have the same meaning as indicated for compound (I), in the form of a racemic or optically active compound wherein, if n is 1, the methyl in position 9a and the hydrogen atom in position 5a is in a relative trans configuration;

in order to obtain an aldehyde of formula

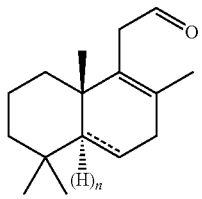

(III)

wherein the dotted line and n have the same meaning as indicated for compound (I), in the form of a racemic or optically active compound wherein, if n is 1, the methyl in position 9a and the hydrogen atom in position 5a is in a relative trans configuration;

B) the reduction of the aldehyde of formula (III), obtained under step A), into the corresponding alcohol of formula

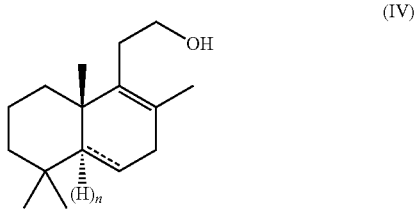

(IV)

wherein the dotted line and n have the same meaning as indicated for compound (I) and, if n is 1, being in the form of a racemic or optically active diastereoisomer wherein the methyl in position 9a and the hydrogen atom in position 5a are in the relative trans configuration;

C) the cyclisation of the compound (IV), obtained under step B), into the corresponding furan of formula (I), as defined above.

For the sake of clarity, it is understood that by the expression "in the form of a racemic or optically active diastereoisomer/compound" it is intended that said diastereoisomer or compound of formula (I) to (IV) has an enantiomeric excess (e.e.) ranging from 0 to 100%. For example a specific compound (I) can be in the form of any mixture of the two enantiomers of formulae (A) or (B)

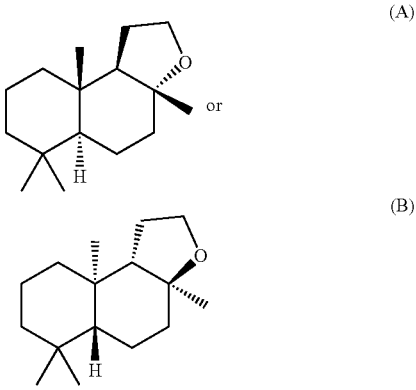

(A)

or (B)

wherein the indicated stereochemistry is absolute.

As well known by a person skilled in the art, it is understood that when the invention's process is used to obtain a compound (I) in an optically active form, then the corresponding compounds (II) to (IV) used as starting material or intermediates need to have an adequate optical activity.

As typical examples of compounds (I) one may cite the following:
(3aR,9aR,9bR)-3a,6,6,9a-tetramethyl-1,2,3a,4,6,7,8,9,9a, 9b-decahydronaphtho[2,1-b]furan,
(3aRS,9aRS,9bRS)-3a,6,6,9a-tetramethyl-1,2,3a,4,6,7,8,9, 9a,9b-decahydronaphtho[2,1-b]furan,
(3aS,9aS,9bS)-3a,6,6,9a-tetramethyl-1,2,3a,4,6,7,8,9,9a,9b-decahydronaphtho[2,1-b]furan,
(3aR,5aS,9aS,9bR)-3a,6,6,9a-tetramethyldodecahydronaphtho[2,1-b]furan,
(3aRS,5aSR,9aSR,9bRS)-3a,6,6,9a-tetramethyldodecahydronaphtho[2,1-b]furan or
(3aS,5aR,9aR,9bS)-3a,6,6,9a-tetramethyldodecahydronaphtho[2,1-b]furan.

Compound (II) is a known compound, and its preparation is reported by C. Fehr et al., in *Org. Lett.*, 2006, 8, 1839, or by Danieswski et al. in *J. Org. Chem.*, 1985, 50, 3963. The enantiomerically pure compound (II) can be obtained according to the method reported in *Org. Lett.*, 2006, 8, 1839, and using an optically active precursor (disclosed in WO 07/010, 420).

The compounds of formula (III) and (IV), wherein the dotted line represents a double bond, in the form of any one of its stereoisomers or mixture thereof, are new compounds. Therefore, being valuable intermediates of the invention's process, said compounds are other objects of the present invention.

Specific examples of said novel compounds are 2-(2,5,5, 8a-tetramethyl-3,5,6,7,8,8a-hexahydro-1-naphthalenyl) ethanol or (2,5,5,8a-tetramethyl-3,5,6,7,8,8a-hexahydro-1-naphthalenyl)acetaldehyde.

The first step of the invention's process is Step A). It can be carried out by reacting compound (II) with catalysts of the vanadyl type or molybdenum oxide derivatives.

Examples of such catalysts are the ones of formula $V(O)(OR)_3$ or $MoO_2X_2$, wherein R represents a $C_1$-$C_9$ alkyl or phenyl group or a $C_1$-$C_9$ silyl phenyl group, and X represents a Cl, NCS, an acetylacetonate or a $C_1$-$C_9$ alcoholate or phenolate. Examples of such catalysts are reported in *Tet. Lett.*, 1996, 37, 853 or in *Tet. Lett.*, 1976, 2981. As non-limiting examples, one may cite $VO(OSiPh_3)_3$ or its polymeric form $[VO(OSiPh_2)]_n$, $[V_2O_6SiPh_2]_n$, $MoO_2Cl_2$ or $MoO_2(acac)_2$.

It is worth noting that said transformation is not trivial, since many other rearrangement products could have been obtained instead of the required compound (III), in particular when the starting propargylic alcohol is a compound wherein the dotted line represents a double bond (e.g. see C. Fehr et al. in *Org. Lett.*, 2006, 8, 1839).

This process of the invention, in any of its embodiments, can be carried out in the presence or in the absence of solvent, but in any case it is advantageously performed under anhydrous conditions. As a person skilled in the art can anticipate, the presence of a solvent is mandatory only in the case in which the starting compound is a solid under the reaction conditions.

However, according to a preferred embodiment of the invention, the process is advantageously carried out in the presence of a solvent. A suitable solvent is one which is high boiling (e.g. b.p. above 100° C.) and aprotic. Non-limiting examples of such a solvent are ethers, esters, amides, aromatic hydrocarbons, linear or branched or cyclic hydrocarbons, chlorinated solvents and mixtures thereof. More preferably, the solvent is a xylene or o-dichlorobenzene and mixtures thereof.

The temperature, at which this process of the invention can be carried out, in any of its embodiments, is comprised between 60° C. and 200° C., preferably between 120° C. and 160° C. Of course a person skilled in the art is also able to select the preferred temperature as a function of the melting and boiling point of the starting and final products and/or an eventual solvent.

Step B) can be carried out by reacting compound (II) with any reducing agent known by a person skilled in the art to reduce an aldehyde into the corresponding to alcohol, without reducing in a significant amount the carbon-carbon double bond. As non-limiting examples, one may cite hydrides such as $NaBH_4$ or $LiAlH_4$, or catalytic hydrogenation such as the one catalyzed by Ru complexes (e.g. see WO02/22526, WO02/40155 or even *Angew. Chem. Int. Ed.*, 2001, 40, 40 or *Acc. Chem. Res.*, 1997, 30, 97).

This process of the invention, in any of its embodiments, can be carried out in the presence or in the absence of solvent. However, according to a preferred embodiment of the invention, the process is advantageously carried out in the presence of a solvent compatible with the reducing agent, as well known by a person skilled in the art. For instance, one may cite $C_4$-$C_6$ ether, such as ether or THF, when using $LiAlH_4$ as reducing agent. The temperature at which this process of the invention can be carried out, in any of its embodiments, is comprised between $-80°$ C. and $100°$ C., preferably between $-78°$ C. and $50°$ C. Of course a person skilled in the art is also able to select the preferred temperature as a function of the melting and boiling point of the starting and final products and/or an eventual solvent.

Step C) can be carried out by reacting compound (II) with at least one Lewis acid and optionally an additive.

Said Lewis acid can be used in stoechiometric or in catalytic amounts, relative to the starting alcohol.

Useful Lewis acids can be acidic clays, $BF_3$ derivatives or metal salts of formula, $AlCl_2R$, $MX_3$ or $ZnX_2$, wherein R is a $C_1$-$C_4$ alkyl group, M is a trivalent metal cation selected from the group consisting of Al, Y, Sc and Fe, and X represents a Cl or F atom or is a weakly or non-coordinating mono anion.

Said acids can be in an anhydrous form or for some of them also in a hydrate form. Furthermore, the boron or aluminum derivative, especially $BF_3$, could be in the form of any one of its adducts with an ether or carboxylic acid, such as $R^1_2O$ or $R^2COOH$, wherein $R^1$ is a $C_1$-$C_5$ alkyl group, such as $C_2H_5$ or $C_4H_9$, and $R^2$ is a $C_1$-$C_{20}$ alkyl group, such a methyl, ethyl or hept-3-yl.

Non limiting examples of acidic clays are, for instance, clays of the F-20X type.

Non-limiting examples of suitable weakly or non-coordinating mono anions are $ClO_4^-$, $C_{1-8}$ sulfonates, $BF_4^-$, $PF_6^-$, $SbCl_6^-$, $AsCl_6^-$, $SbF_6^-$, $AsF_6^-$ or $BR^4_4^-$, wherein $R^4$ is a phenyl group optionally substituted by one to five groups such as halide atoms or methyl or $CF_3$ groups. According to a particular embodiment of the invention, X is $BF_4^-$, $PF_6^-$, $C_6F_5SO_3^-$, $CF_3SO_3^-$, $MeSO_3^-$, $MeC_6H_4SO_3^-$ or $Cl^-$.

According to a further particular embodiment of the invention, preferred Lewis acids are $BF_3$ or a $BF_3$ adduct with a $C_1$-$C_4$ ether or carboxylic acid (such as $Et_2O$, $Bu_2O$ or AcOH), $FeX_3$ or $ScX_3$, X being as defined above.

As specific examples, but not limiting, of Lewis acids one may cite acids such as $FeCl_3$, $Sc(CF_3SO_3)_3$, or $BF_3(Et_2O)_2$.

Additives can be used, e.g. to increase the selectivity and/or the yield of the cyclisation.

As additive can be used a $C_0$-$C_8$ sulphonic acid, water, a $C_1$-$C_{12}$ alcohol, silica, aluminium oxide or molecular sieves. According to a particular embodiment said additive can be acidic or neutral, and in the form of small particles, or even a powder.

Typical examples are butanol, neutral alumina, silica gel (e.g. of the type commonly used for chromatography), or molecular sieves 4 Å. Typical examples of sulphonic acids are $FSO_3H$, $MeSO_3H$, $MeC_6H_4SO_3H$ and the similar.

According to a particular embodiment, for the cyclisation a combination of $FeCl_3$ and silica can be used. Alternatively a combination of $FeCl_3$ and $C_0$-$C_8$ sulphonic acid or a combination of $FeCl_3$ and butanol can be used.

The Lewis acid can be added to the reaction medium in a large range of concentrations. As non-limiting examples, one can cite catalyst concentrations ranging from 0.01 to 1.50 molar equivalents, relative to the molar amount of the starting alcohol (IV). Preferably, the Lewis acid concentration will be comprised between 0.1 and 0.6 molar equivalents. It goes without saying that the optimum concentration of acid will depend on the nature of the latter and on the desired reaction time.

The additive can be added to the reaction medium in a large range of concentrations. As non-limiting examples, one can cite additive concentrations ranging from 10 to 250%, relative the weight of the Lewis acid. Preferably, the additive concentration will be comprised between 10 and 120%, relative the weight of the Lewis acid.

Step C) of the invention's process, in any of its embodiments, can be carried out in the presence or in the absence of solvent, but in any case it is advantageously to performed under anhydrous conditions.

However, according to a preferred embodiment of the invention, the process is advantageously carried out in the presence of a solvent. A suitable solvent is one which is aprotic. Non-limiting examples of such a solvent are ethers, esters, amides, aromatic hydrocarbons, linear or branched or cyclic hydrocarbons, chlorinated solvents and mixtures thereof. More preferably, the solvent is a methylene chloride, 1,2-dichloroethane, 1,2-dichlorobenzene, toluene and mixtures thereof.

The temperature at which this process of the invention can be carried out, in any of its embodiments, is comprised between $-50°$ C. and $140°$ C., preferably between $-10°$ C. and $80°$ C. Of course a person skilled in the art is also able to select the preferred temperature as a function of the melting and boiling point of the starting and final products and/or an eventual solvent.

Alternatively, if it is used a compound (II) wherein the dotted line represents a single bond, the cyclisation can be carried out by using a strong protic acid (i.e. $pK_a<1$). This type of cyclisation is, per se, known by a person skilled in the art and does not need to be discussed in further detail. However, one may cite as non-limiting examples of protic acids, $MeSO_3H$, $CF_3COOH$ or $MeC_6H_4SO_3H$. Typical conditions for the cyclisation are reported in A. De Groot et al, *Tetrahedron*, 1994, 50, 10095.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in $CDCl_3$ with a 360 MHz or 100 MHz machine for $^1H$ or $^{13}C$ respectively, the chemical displacements 6 are indicated in ppm with respect to TMS as standard, the coupling constants J are expressed in Hz.

Example 1

Preparation of (3aRS,9aRS,9bRS)-3a,6,6,9a-tetramethyl-1,2,3a,4,6,7,8,9,9a,9b-decahydronaphtho[2,1-b]furan (1)

Step A)

A solution of 1-ethynyl-2,5,5,8a-tetramethyl-1,2,3,5,6,7,8,8a-octahydro-1-naphthalenol (4.00 g; 17.2 mmol) in o-xylene (60 ml) was treated with $[V_2O_6SiPh_2]_n$ (400 mg) [*Tetrahedron Lett.* 1976, 17, 2981] and heated at reflux (145° C.). After 17 hours, the rearrangement was complete. The reaction mixture was poured into 5% aquous NaOH. The product was extracted twice with $Et_2O$ and washed successively with $H_2O$ and twice with satured aqueous NaCl, dried (Na$_2$SO$_4$) and evaporated. Bulb-to-bulb distillation (125° C. (oven temp.)/ 0.04 mbar) afforded 97% pure (2,5,5,8a-tetramethyl-3,5,6,7, 8,8a-hexahydro-1-naphthalenyl)acetaldehyde (3.42 g; yield=83%).

$^1$H-NMR: 1.13 (s, 3H), 1.14 (s, 3H), 1.77 (s, 3H), 1.10-1.35 (m, 2H), 1.42-1.60 (m, 2H), 1.65 (s, 3H), 1.70-1.85 (m, 2H), 2.62-2.72 (m, 2H), 3.11 (d, J=17 Hz, 1H), 3.22 (d, J=17 Hz, 1H), 5.66 (m, 1H), 9.55 (t, J=2 Hz, 1H).

$^{13}$C-NMR: 201.4 (d), 148.3 (s), 129.6 (s), 129.4 (s), 117.1 (d), 43.3 (t), 40.6 (t), 39.2 (s), 37.5 (t); 36.1 (s), 33.6 (t), 32.8 (q), 30.5 (q); 25.8 (q), 19.6 (q), 18.7 (t).

Step B)

A solution of (2,5,5,8a-tetramethyl-3,5,6,7,8,8a-hexahydro-1-naphthalenyl)acetaldehyde obtained in step A) (3.40 g; 14.2 mmol) in Et$_2$O (10 ml) was added drop-wise to a stirred suspension of LiAlH$_4$ (410 mg; 10.7 mmol) in Et$_2$O (20 ml) at such a rate that a gentle reflux was maintained (5 minutes). The suspension was heated at reflux for 30 minutes, cooled at 0° C. and treated successively drop-wise with water (0.4 ml), 5% aqueous NaOH (0.4 ml) and water (3×0.4 ml). After stiffing for 5 minutes at room temperature the suspension was filtered over Celite and the filtrate concentrated. Bulb-to-bulb distillation (130° C. (oven temp.)/0.03 mbar) afforded pure 2-(2,5,5,8a-tetramethyl-3,5,6,7,8,8a-hexahydro-1-naphthalenyl)ethanol (2) (3.21 g; yield=90%).

$^1$H-NMR: 1.12 (s, 3H), 1.14 (s, 3H), 1.16 (s, 3H), 1.22-1.38 (m, 2H), 1.45 (m, 1H), 1.55 (m, 1H), 1.70 (s, 3H), 1.72-1.85 (m, 2H), 1.91 (m, 1H), 2.30 (m, 1H), 2.51 (m, 1H), 2.52-2.65 (m, 2H), 3.63 (m, 2H), 5.63 (m, 1H).

$^{13}$C-NMR: 149.0 (s), 133.8 (s), 127.0 (s), 117.1 (d), 62.6 (t), 40.7 (t), 39.5 (s), 37.0 (t), 36.0 (s); 33.5 (t), 32.8 (q), 31.6 (t), 30.9 (q); 26.0 (q), 19.6 (q), 18.8 (t).

Step C)

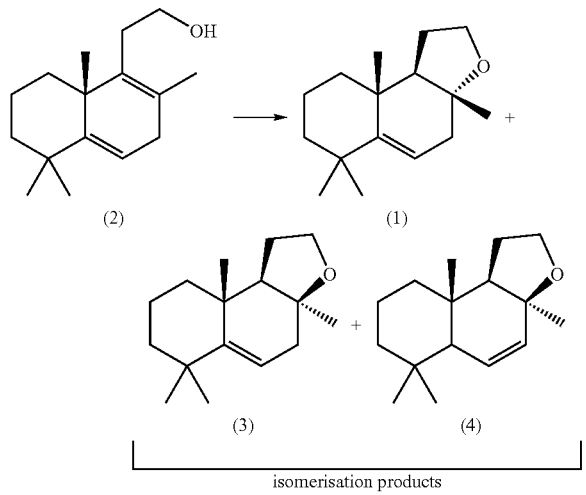

Using FeCl$_3$ and SiO$_2$:

A solution of 2-(2,5,5,8a-tetramethyl-3,5,6,7,8,8a-hexahydro-1-naphthalenyl)ethanol (500 mg; 96% pure; 2.05 mmol) in 1,2-dichloroethane (5 ml) and CH$_2$Cl$_2$ (8 ml) was treated at 24° C. with SiO$_2$ 60 Å (70-220 μm) (84 mg). Under stiffing FeCl$_3$ (glove-box stored; 167 mg; 1.03 mmol) was added. After 20 min the dark reaction mixture was poured under stirring into 5% HCl and was extracted with Et$_2$O (2×). The organic phase was washed successively with water, sat. aq. NaHCO$_3$ and saturated aqueous NaCl, dried (Na$_2$SO$_4$) and evaporated. Bulb-to-bulb distillation (125° C. (oven temp.)/0.06 mbar) afforded (±)-(1) (454 mg; 81% pure; yield=73%). It was also obtained (3) (yield=4%) and (4) (yield=2%).

It was also recovered (2) (yield=8%).

Using FeCl$_3$ in Stoichiometric Amounts:

A solution of 2-(2,5,5,8a-tetramethyl-3,5,6,7,8,8a-hexahydro-1-naphthalenyl)ethanol (300 mg; 1.28 mmol) in CH$_2$Cl$_2$ (4 ml) and 1,2-dichloroethane (2 ml) was treated at 0° C. with FeCl$_3$ (208 mg; 1.28 mmol). After 40 minutes the conversion was completed.

The reaction mixture was poured under stiffing into 5% aqueous HCl and was extracted twice with Et$_2$O. The organic phase was washed successively with water, saturated aqueous NaHCO$_3$ and twice with saturated aqueous NaCl, dried (Na$_2$SO$_4$) and evaporated. Bulb-to-bulb distillation (115° C. (oven temp.)/0.03 mbar) afforded pure (±)-(1) (198 mg; 96% pure; yield=63%) containing traces of (3) (yield=2%).

Using FeCl$_3$ in Catalytic Amounts:

A solution of (+)-2-(2,5,5,8a-tetramethyl-3,5,6,7,8,8a-hexahydro-1-naphthalenyl)ethanol* ([α]$_D^{20}$+45 (CHCl$_3$; c: 0.84; 1.0 g; 4.27 mmol) in 1,2-dichloroethane (20 ml) was treated at 0° C. with anhydrous FeCl$_3$ (138 mg; 0.848 mmol). After 2 minutes, the temperature was allowed to reach room temperature. Stirring was continued for 3 hours, then another portion of anhydrous FeCl$_3$ (69 mg; 0.424 mmol) was added and stiffing continued for 30 minutes. The reaction mixture was stopped at partial conversion by pouring it under stiffing into 5% aqueous HCl and was extracted twice with Et$_2$O. The organic phase was washed successively with water, saturated aqueous NaHCO$_3$ and twice with saturated aqueous NaCl, dried (Na$_2$SO$_4$) and evaporated. Purification by column chromatography (SiO$_2$ (60 g); cyclohexane/AcOEt=99:1), afforded 159 mg of first fractions (containing appreciatively 39% of (+)-(1), 27% of (3) and 9% of (+)-(4)), followed by 423 mg (yield=42%) of pure (+)-(1) (93% ee; [α]$_D^{20}$+84 (CHCl$_3$; c: 0.92; 739 mg) and then using cyclohexane/ AcOEt=9:1, 316 mg (yield=32%) of (+)-(2) were recovered.

* prepared from (−)-2-methyl-4-(2,6,6-trimethyl-1-cyclohexen-1-yl)butanal prepared according the procedure described in WO 2007/010420

Example 2

Preparation of (3aRS,5aSR,9aSR,9bRS)-3a,6,6,9a-tetramethyldodecahydronaphtho[2,1-b]furan (5)

Step A)

A solution of 1-ethynyl-2,5,5,8a-tetramethyl-perhydro-4aH-1-naphthalenol (8.48 g; 92% pure; 33.3 mmol) in o-xylene (40 ml) was added drop-wise in 20 minutes to a refluxing mixture (145° C.) of [Ph$_3$SiO]$_3$VO (1.79 g; 2.00 mmol), triphenylsilanol (1.38 g; 5.00 mmol) and stearic acid (191 mg; 0.67 mmol) in o-xylene (40 ml). After 7 hours the reaction mixture was poured into 5% aqueous NaOH. The product was extracted twice with Et$_2$O and washed successively with H$_2$O and twice with saturated aqueous NaCl, dried (Na$_2$SO$_4$) and evaporated. Bulb-to-bulb distillation (125° C. (oven temp.)/ 0.03 mbar) afforded 87% pure (2,5,5,8aβ-tetramethyl-3,4, 4aα,5,6,7,8,8a-octahydro-1-naphthalenyl)acetaldehyde (7.59 g; yield=85%).

Using [V$_2$O$_6$SiPh$_2$]$_n$, as for Example 1, Step A), also afforded (2,5,5,8aβ-tetramethyl-3,4,4aα,5,6,7,8,8a-octahydro-1-naphthalenyl)acetaldehyde in 85% yield.

$^{13}$C-NMR: 201.5 (d), 132.1 (s), 131.3 (s), 51.7 (d), 43.2 (t), 41.5 (t), 38.5 (s), 37.2 (t), 33.9 (t); 33.3 (s), 33.2 (q), 21.6 (q), 19.9 (q); 19.8 (q), 18.9 (t), 18.9 (t).

Step B)

A solution of (2,5,5,8aβ-tetramethyl-3,4,4aα,5,6,7,8,8a-octahydro-1-naphthalenyl)acetaldehyde (7.58 g; 87% pure; 28.2 mmol) in Et$_2$O (50 ml) was added drop-wise to a stirred suspension of LiAlH$_4$ (800 mg; 21.1 mmol) in Et$_2$O (20 ml) at such a rate that a gentle reflux was maintained (5 minutes). The suspension was heated at reflux for 30 minutes, cooled at 0° C. and treated successively drop-wise with water (0.8 ml), 5% aqueous NaOH (0.8 ml) and water (3×0.8 ml). After stirring for 5 minutes at room temperature, the white suspension was filtered over Celite and the filtrate concentrated. Bulb-to-bulb distillation (130° C. (oven temp.)/0.03 mbar) afforded 94% pure 2-(2,5,5,8aβ-tetramethyl-3,4,4aα,5,6,7,8,8a-octahydro-1-naphthalenyl)ethanol (6) (6.98 g; 94% pure; yield=99%).

$^{13}$C-NMR: 136.2 (s), 128.6 (s), 62.7 (t), 51.7 (d), 41.7 (t), 38.7 (s), 37.2 (t), 33.7 (t), 33.3 (s); 33.3 (q), 31.5 (t), 21.7 (q), 20.1 (q); 19.9 (q), 19.0 (t), 19.0 (t).

Step C)

(6)  →  (5)  +

(7)

isomerisation products

Using FeCl$_3$ and SiO$_2$:

A solution of 2-(2,5,5,8aβ-tetramethyl-3,4,4aα,5,6,7,8,8a-octahydro-1-naphthalenyl)ethanol (500 mg; 94% pure; 1.99 mmol) in 1,2-dichloroethane (5 ml) and CH$_2$Cl$_2$ (8 ml) was treated at 24° C. with SiO$_2$ 60 Å (70-220 μm) (81 mg). Under stiffing anhydrous FeCl$_3$ (162 mg; 1.00 mmol) was added. After 20 minutes the dark reaction mixture was poured under stiffing into 5% aqueous HCl and was extracted twice with Et$_2$O. The organic phase was washed successively with water, saturated aqueous NaHCO$_3$ and twice with saturated aqueous NaCl e, dried (Na$_2$SO$_4$) and evaporated (513 mg). Bulb-to-bulb distillation (125° C. (oven temp.)/0.06 mbar) afforded (5) (481 mg; 77% pure; yield=79%), containing recovered (6) (yield=13%).

Example 3

Following the same experimental procedure as described in Example 2, other Lewis acids have been tested.

The results for the cyclisation of (2) are reported in the following Table I:

| N° | Lewis acid[1] | Additive[2] | Solvent[3] | T (° C.) | t[4] | Res.[5] | (6)[6] | (5)[6] | (7)[6] | (5)/(7)[7] |
|---|---|---|---|---|---|---|---|---|---|---|
| 1 | Sc(OTf)$_3$ (0.2) | — | CH$_2$Cl$_2$ | 20 | 6 h. | | 60 | 30 | 0 | >100 |
| 2 | FeCl$_3$ (0.25) | — | (ClCH$_2$)$_2$ | 20 | 3 h | | 32 | 57 | 1 | 57 |
| 3 | FeCl$_3$ (0.50) | — | (ClCH$_2$)$_2$CH$_2$Cl$_2$ (½) | 10 | 3 h | 23 | 11 | 78 | 0 | >100 |
| 4 | FeCl$_3$ (0.50) | SiO$_2$ (50%) | (ClCH$_2$)$_2$CH$_2$Cl$_2$ (½) | 20 | 20 min. | 6 | 11 | 77 | 1 | 77 |
| 5 | FeCl$_3$ (0.50) | SiO$_2$ (50%) | toluene | 20 | 2 h. | 6 | 13 | 74 | 2 | 37 |
| 6* | MeSO$_3$H (1.28) | — | CH$_2$Cl$_2$ | 0° | 20 min. | 12 | 2 | 81 | 5 | 16 | p.s. it was used the starting material obtained in Example 1 (94% purity)

[1] between brackets is the molar amount relative to starting alcohol (6)

[2] between brackets is the w/w amount relative to Lewis acid

[3] the w/w ratio between (6) and the solvent is the same as in Example 2), between brackets it is the w/w ratio between two solvents

[4] reaction time

[5] non-volatile products recovered other than (6), (5) and (7), w/w percentage relative to the amount of (6) initially used (%)

[6] relative amounts obtained by GC analysis of the volatile fraction (%)

[7] molar ratio

OTf = triflate

*comparative example (prior art conditions - WO 06/10287)

The results for the cyclisation of a mixture of isomers of formula (IV) are reported in the following Table II:

| N° | Lewis acid[1] | Additive[2] | Solvent[3] | T (°C.) | t[4] | Res.[5] | SM[6] | (5)[6] | (7)[6] | (5)/(7)[7] |
|---|---|---|---|---|---|---|---|---|---|---|
| 1 | FeCl$_3$ (0.50) | SiO$_2$ (50%) | (ClCH$_2$)$_2$ | 20 | 40 min. | 3 | 18 | 73 | 4 | 18 |
| 2 | FeCl$_3$ (0.2) | MeSO$_3$H (0.2)** | (ClCH$_2$)$_2$CH$_2$Cl$_2$ (½) | 20 | 10 min. | 2 | 9 | 79 | 6 | 13 |
| 3 | MeSO$_3$H (1.28) | — | CH$_2$Cl$_2$ | 20 | 45 min. | 8 | 23 | 67 | 6 | 11 |

SM: starting alcohol
[1] between brackets is the molar amount relative to starting alcohol
[2] between brackets is the w/w amount relative to Lewis acid;
**molar amount relative to starting alcohol
[3] the w/w ratio between SM and the solvent is the same as in Example 2), between brackets it is the w/w ratio between two solvents
[4] reaction time
[5] non-volatile products recovered other than starting alcohol, (5) and (7), w/w percentage relative to the amount of alcohol initially used (%)
[6] relative amounts obtained by GC analysis of the volatile fraction (%)
[7] molar ratio
OTf = triflate
*comparative example (prior art conditions - WO 06/10287)

The results for the cyclisation of (2) are reporting in the following Table III:

| N° | Lewis acid[1] | Additive[2] | Solvent[3] | T (°C.) | t[4] | (2)[5] | (1)[5] | (4) + (3)[5] |
|---|---|---|---|---|---|---|---|---|
| 1 | FeCl$_3$ (0.25) | — | (ClCH$_2$)$_2$ | 20 | 3.5 h. | 7 | 68 | 11 |
| 2 | FeCl$_3$ (0.50) | SiO$_2$ (50%) | (ClCH$_2$)$_2$CH$_2$Cl$_2$ (½) | 20 | 20 min. | 8 | 81 | 6 |
| 3 | Sc(OTf)$_3$ (0.2) | — | CH$_2$Cl$_2$ | 20 | 3 h. | 21 | 56 | 12 |
| 4 | BF$_3$(OEt)$_2$ (1.1) | — | CH$_2$Cl$_2$ | 20 | 4 h. | 29 | 61 | 4 | p.s. it was used the starting material obtained in Example 1 (94% purity)
[1] between brackets is the molar amount relative to starting alcohol (2)
[2] between brackets is the w/w amount relative to Lewis acid
[3] the w/w ratio between (2) and the solvent is the same as in Example 2), between brackets it is the w/w ratio between two solvents
[4] reaction time
[5] relative amounts obtained by GC analysis of the volatile fraction (%)
OTf = triflate When the cyclisation of (2) with MeSO$_3$H (prior art conditions—WO 06/10287) was attempted (1.3 molar equivalent, T 20° C.) a very complex mixture was obtained, wherein the desired furan (1) accounted for less than 5% of the total and many unknown products were obtained (accounting for more than 30%).

The same cyclisation with ClSO$_3$H (1.0 molar equivalent, T −78° C., MeNO$_2$) afforded only a rearrangement product (3a,5a,6,6-tetramethyl-1,2,3a,4,5,5a,6,7,8,9-perhydronaphtho[2,1-b]furan) in about 25% yield.

What is claimed is:
1. A process for the preparation of a furan of formula

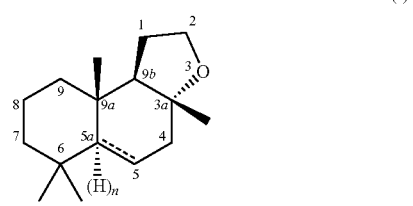

(I)

wherein the dotted line is a single bond and n is 1 or the dotted line is a double bond and n is 0, in the form of a racemic or optically active diastereoisomer, wherein the substituents in the positions 9a, 9b and 3a are in a relative configuration cis, and the hydrogen atom in position 5a and the oxygen atoms are in configuration trans relative to the methyl in position 9a;
wherein the process comprises:
A) rearranging a propargylic alcohol of formula

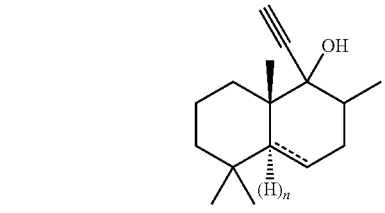

(II)

wherein the dotted line and n have the same meaning as indicated for compound (I), in the form of a racemic or optically active compound wherein, if n is 1, the methyl in position 9a and the hydrogen atom in position 5a is in a relative trans configuration;

to obtain an aldehyde of formula

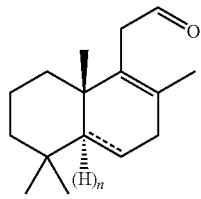
(III)

wherein the dotted line and n have the same meaning as indicated for compound (I), in the form of a racemic or optically active compound wherein, if n is 1, the methyl in position 9a and the hydrogen atom in position 5a is in a relative trans configuration;

B) reducing the aldehyde of formula (III) into the corresponding alcohol of formula

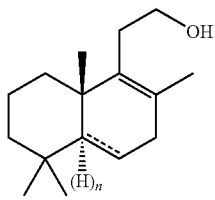
(IV)

wherein the dotted line and n have the same meaning as indicated for compound (I) and, if n is 1, being in the form of a racemic or optically active diastereoisomer wherein the methyl in position 9a and the hydrogen atom in position 5a are in the relative trans configuration;

C) cyclizing compound (IV) into the corresponding furan of formula (I).

2. The process according to claim 1, wherein the compound of formula (I) is a compound wherein the dotted line represents a double bond and n is 0.

3. The process according to claim 1, wherein the compound of formula (I) is optically active.

4. The process according to claim 1, wherein A) is carried out by reacting compound (II) with a vanadyl or molybdenum oxide catalyst.

5. The process according to claim 1, wherein B) is carried out by reacting compound (II) with a reducing hydride or by catalytic hydrogenation using an appropriate Ru complex.

6. The process according to claim 1, wherein C) is carried out by reacting compound (II) with at least one Lewis acid.

7. The process according to claim 6, wherein the Lewis acid is selected from the group consisting of acidic clays, $BF_3$ derivatives, and metal salts of formula $AlCl_2R$, $MX_3$ or $ZnX_2$, wherein R is a $C_1$-$C_4$ alkyl group, M is a trivalent metal cation selected from the group consisting of Al, Y, Sc and Fe, and X represents a Cl or F atom or is a weakly or non-coordinating mono anion.

8. The process according to claim 7, wherein X is selected from the group consisting of $ClO_4^-$, $C_{1-8}$ sulfonates, $BF_4^-$, $PF_6^-$, $SbCl_6^-$, $AsCl_6^-$, $SbF_6^-$, $AsF_6^-$ or $BR^4_4{}^-$, wherein $R^4$ is a phenyl group optionally substituted by one to five groups such as halide atoms or methyl or $CF_3$ groups.

9. The process according to claim 6, wherein the Lewis acid is selected from the group consisting of $FeCl_3$, $Sc(CF_3SO_3)_3$, and $BF_3 (Et_2O)_2$.

10. The process according to claim 6, wherein C) is carried out by reacting compound (II) with at least one Lewis acid and at least one additive of a $C_0$-$C_8$ sulphonic acid, water, a $C_1$-$C_{12}$ alcohol, silica, aluminium oxide or a molecular sieve.

11. The process according to claim 1, wherein when the dotted line is selected to be a single bond and n is 1, then C) is carried out by reacting compound (II) with at least one strong protic acid.

12. A compound of formula

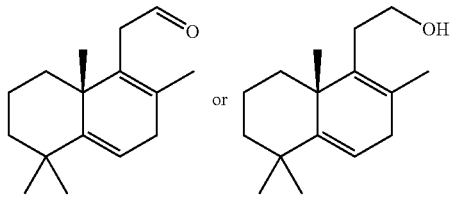

in the form of any one of its stereoisomers or mixtures thereof.

* * * * *